United States Patent [19]
Philippe et al.

[11] Patent Number: 5,869,711
[45] Date of Patent: Feb. 9, 1999

[54] CERAMIDE COMPOUNDS, PROCESS FOR THEIR PREPARATION AND USE

[75] Inventors: Michel Philippe, Wissous; Bernadette Luppi, Sevran; Didier Semeria, Courtry, all of France

[73] Assignee: L'Oreal, Paris, France

[21] Appl. No.: 628,169

[22] Filed: Apr. 5, 1996

[30] Foreign Application Priority Data

Apr. 5, 1995 [FR] France .................................. 95 04050

[51] Int. Cl.$^6$ ................................................ C07C 233/00
[52] U.S. Cl. ........................... 554/66; 564/201; 564/203
[58] Field of Search .............................. 554/66; 564/201, 564/203; 514/625, 627; 424/401

[56] References Cited

U.S. PATENT DOCUMENTS

| | | | |
|---|---|---|---|
| 5,368,857 | 11/1994 | Corcoran et al. | 424/401 |
| 5,525,709 | 6/1996 | Davey et al. | 554/68 |
| 5,543,431 | 8/1996 | Bolessa et al. | 514/627 |
| 5,589,178 | 12/1996 | Aubert et al. | 424/401 |
| 5,631,356 | 5/1997 | Smeets et al. | 536/18.6 |

FOREIGN PATENT DOCUMENTS

| | | |
|---|---|---|
| 0 500 437 | 8/1992 | European Pat. Off. |
| WO 93/20038 | 10/1993 | WIPO |

OTHER PUBLICATIONS

Lambers et al., Chemical Abstracts, vol. 124, abstract 176810, 1995.
De Patert et al., Chemical Abstracts, vol. 124, abstract 117888, 1995.
Wild et al., Chemical Abstracts, vol. 123, abstract 228693x, 1995.
K. Sisido et al., "Synthesis of All the Racemic Diastereoisomers of Phytosphingosine" Journal Of Organic Chemistry, vol. 35, No. 2, (1970) pp. 350–353.
K. Sisido et al., "Synthesis of racemic Phytosphingosine and the lyxo Isomer" Journal Or Organic Chemistry, vol. 34, No. 11, (1969) pp. 3539–3544.
Chemical Abstracts, Abstract No. 175530, vol. 121, No. 5 (1994).
Chemical Abstracts, Abstract No. 25005, vol. 117, No. 3, (1992).
Chemical Abstracts, Abstract No. 179361, vol. 15, No. 17, (1991).
R. Kraus et al., "Ceramides From Urtica Dioica Roots" Lieb. Ann. Chem., (1991) pp. 125–128.
Chemical Abstracts, Abstract No. 73760, vol. 112, No. 9, (1990).
Chemical Abstracts, Abstract No. 35441, vol. 103, No. 5, (1985).
Chemical Abstracts, Abstract No. 85024, vol. 75, No. 13, (1971).

*Primary Examiner*—Richard L. Raymond
*Attorney, Agent, or Firm*—Finnegan, Henderson, Farabow, Garrett & Dunner, L.L.P.

[57] ABSTRACT

The present invention relates to compounds corresponding to the formula:

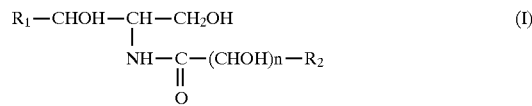

the compounds being in the form of mixtures of isomers at least on the amino alcohol part of the said formula (I). The invention also relates to a process for their preparation and their use, in particular for the treatment and care of the skin, the hair, the nails and the eyelashes in cosmetics or in dermatology.

17 Claims, No Drawings

CERAMIDE COMPOUNDS, PROCESS FOR THEIR PREPARATION AND USE

The present invention relates to novel mixtures of ceramide compounds, to a process for their preparation and to their use, in particular for the treatment and care of the skin, the hair, the nails and the eyelashes in cosmetics or in dermatology.

Exposure of the skin to the cold, to the sun, to atmospheres of low relative humidity, repeated treatments with washing compositions and contact with organic solvents are factors which lead, in varying degrees, to visible drying. The skin appears drier and less supple, and the cutaneous relief is more pronounced. Moreover, hair which is subjected too often to certain hair treatments loses its shiny appearance and may become coarse and brittle. The Inventors have thus sought compounds which make it possible to prevent or correct these phenomena reflected by a visible drying and which restore flexibility to the skin and shine and softness to the hair. It has already been proposed to use ceramides to overcome this problem. Indeed, it is known that these compounds are the predominant constituent elements of the intercorneocytic lipids of the stratum corneum and contribute towards maintaining the integrity of the skin barrier.

The ceramides used in cosmetics are usually natural extracts derived in particular from pigskin, cow brain, eggs, blood cells, plants such as wheat, etc. (Japanese patent applications J 86/260008 and J 87/120308). Such ceramides have also been proposed for hair protection (EP 0,278,505).

This therefore always involves mixtures with a larger or smaller content of ceramides and whose composition is difficult to control. Furthermore, these mixtures are subject to bacterial contamination. It is thus difficult to control their storage. When they are of animal origin, there is an additional risk of contamination by the agent responsible for BSE (bovine spongiform encephalopathy).

Each ceramide of natural origin has a specific and unique stereoisomerism, such as those described for sphinganine, phytosphingosine and sphingosine (also referred to as sphingenine) which are, respectively, (2S,3R)-2-amino-1,3-octadecanediol, (2S,3S,4R)-2-amino-1,3,4-octadecanetriol and (2S,3R,4E)-2-amino-4-octadecene-1,3-diol [J. Biochem. 79, 11–21 (1977)].

In order to offer improvements, we have proposed synthetic ceramides, in particular in European patent application No. 0,500,437. When used in cosmetic or dermatological compositions for the treatment and care of the skin and the hair, these compounds have a moisturizing effect which makes it possible to prevent or correct certain effects of visible drying of the skin or the hair.

However, it would be desirable to develop compounds which, when used in cosmetic or dermatological compositions, have a moisturizing or treating effect which is superior to that of the compounds of the above patent application.

Patent application WO 94/10131 should also be noted, this patent application describing a fermentation process which leads to a family of ceramides similar to the ceramides 1 in the Downing classification (J.I.D.-84, 410–412, 1985); this process is thus, unfortunately, restricted to that family of ceramides.

The subject of the present invention thus includes at least two compounds corresponding to the formula:

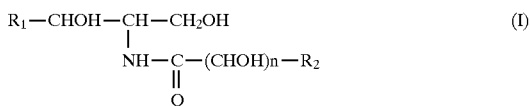

in which:

$R_1$ denotes a saturated or unsaturated $C_{10}$ to $C_{25}$ hydroxylated hydrocarbon radical;

n is equal to 0 or 1;

$R_2$ denotes a linear or branched, saturated or unsaturated $C_1$ to $C_{31}$ hydrocarbon radical, when n is equal to 1; $R_2$ denotes a linear or branched, saturated or unsaturated $C_2$ to $C_{31}$ hydrocarbon radical, when n is equal to 0; said at least two compounds being in the form of a mixture of at least two isomers at least on the amino alcohol part of the formula (I). In other words, the present invention includes, without being limited thereto, a racemic mixture of two compounds corresponding to formula (I), each of said compounds bearing an optical configuration opposite to the other in the amino alcohol part of formula (I), or a mixture of at least two diastereomers corresponding to formula (I), each of the at least two diastereomers having a different optical configuration (considering all chiral centers) from the others in the amino alcohol part.

Thus, these novel compounds have very good skin and/or hair moisturizing power when they are used in cosmetic or dermatological compositions.

When $R_1$ denotes a saturated and hydroxylated hydrocarbon radical, it is preferred for the hydroxyl radical to be in an $\alpha$ position relative to the carbon of the —CHOH— group. This hydroxyl radical may be in a substituted form. This radical may then be represented in particular by a radical of formula —O—CO—CHOH—$R_4$, with $R_4$ denoting a linear or branched, saturated or unsaturated $C_1$ to $C_{31}$ hydrocarbon radical.

When $R_1$ denotes an unsaturated and hydroxylated hydrocarbon radical, it is preferred for $R_1$ to have an ethylenic radical in an $\alpha$ position relative to the carbon of the —CHOH— group. More particularly, at least one, and preferably the hydroxyl radical is in a position $\alpha$ to the ethylenic radical.

$R_1$ preferably denotes a saturated and hydroxylated hydrocarbon radical.

$R_1$ also preferably denotes a hydroxylated, saturated or unsaturated $C_{12}$ to $C_{23}$ hydrocarbon radical.

$R_2$ preferably denotes a linear hydrocarbon, more particularly $C_2$ to $C_{25}$ hydrocarbon, radical.

The compounds according to the invention are thus in the form of mixtures of optical and/or geometrical isomers (mixture of enantiomers and/or diastereoisomers) at least on the amino alcohol part, this differentiating them from natural products which are only in the form of a single isomer.

These novel compounds have the advantage of improving and/or re-establishing the barrier function when they are applied to the skin.

The compounds according to the invention are preferably in the form of a mixture of at least 4 isomers.

The compounds of formula (I) are preferably chosen from 2-N-docosanoylaminooctadecane-1,3,4-triol, 2-N-(2-hydroxyhexadecanoyl)aminooctadecane-1,3,4-triol and 2-N-hexadecanoylaminooctadecane-1,3,4-triol.

Hair treated with these compounds of formula (I) has a shiny appearance, a softer feel, and is less sensitive to water, due to the provision of lipid material uniformly distributed on the scales of the hair. The mechanical properties and liveliness are also improved.

The compounds according to the invention may form vesicles with other lipids.

The compounds according to the invention may be obtained by acylation of the amine function of the compounds of formula (II) or of reactive derivatives thereof, such as, for example, the hydrochloride, with a suitable acylating agent.

Thus, another subject of the invention relates to a process for the preparation of isomeric mixtures of the compounds of formula (I) above, characterized in that it comprises:

(a) the acylation of at least two compounds, in the form of a mixture of at least 2 isomers, of the following formula (II):

in which formula (II), $R_1$ has the same meaning as that given above, or of at least one reactive derivative of these compounds of formula (II), using at least one acylating agent of following formula (III):

in which formula (III), $R_2$ and n have the meanings given above, and X represents a group chosen from the hydroxyl radical, a halogen atom, preferably Br, Cl or I, and a radical of formula OB capable of forming an OH group; A is a group chosen from a halogen atom, a radical of formula —O—COO—$R_5$, a radical of formula $OR_6$, a group

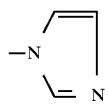

and a group

where $R_5$ is a $C_2$ to $C_8$ lower hydrocarbon radical and $R_6$ is a group chosen from a $C_1$ to $C_8$ lower hydrocarbon radical,

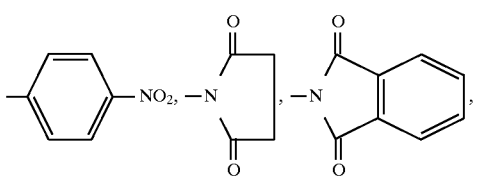

and

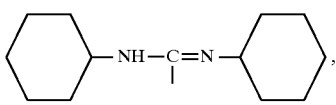

(b) the isolation of the compounds obtained, and
(c) optionally, when X is other than a hydroxyl radical, the hydrolysis or hydrogenolysis of the compounds obtained in order to convert the group OB into a hydroxyl radical, optionally preceded, when X is a halogen atom, by a step of substitution of X with a group OB.

Thus, according to the invention, the term amino alcohol part refers to that part of the formula (I) which comes from the compound of formula (II).

The process is preferably performed in the presence of a suitable solvent. Among the solvents which may be used in the process of the present invention, mention may be made of tetrahydrofuran (THF), pyridine, 1,2-dimethoxyethane, dimethylformamide, dichloromethane and tert-butyl methyl ether.

The group OB is preferably chosen from the following radicals: acetate, benzoate, benzyloxy, —OSi($CH_3$)$_3$, —OSi($CH_3$)$_2$(t-butyl), and —OSi(t-butyl)(—$C_6H_5$)$_2$. Even more preferably, OB is an acetate group.

A is preferably a group chosen from the following groups: —Cl, a radical of formula —O—COO—$C_2H_5$, a radical of formula —OCH$_3$ or —OC$_2H_5$,

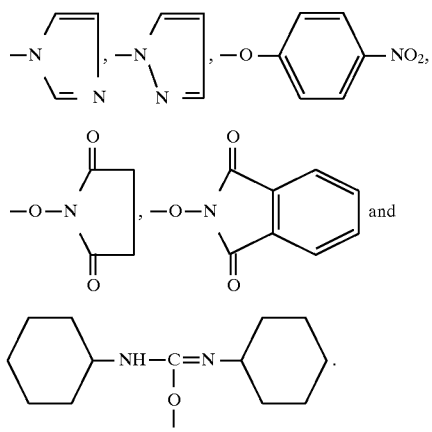

The following radicals are most particularly recommended for A

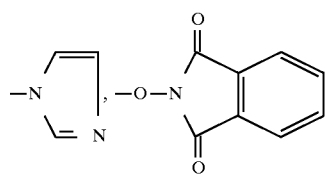

and

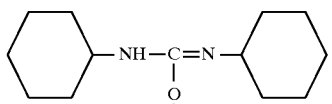

The acylating agents particularly recommended are the succinimide and carbodiimide esters, imidazole derivatives and acid chlorides, as defined above.

It is thus also possible to use salts, such as the hydrochlorides of the compounds of formula (II), for the preparation of the compounds of formula (I).

The compounds of formula (II) or derivatives thereof are known and have been described in particular by M. Prostenik (Croatia Chemica Acta, 29, 107–113, 1957) and M. J äger (Angew. Chem. Int., 603–605, 1981), the disclosures of which are specifically incorporated by reference herein. These compounds are mixtures of at least 2 optical and/or geometrical isomers (enantiomers and/or diastereoisomers).

The acylating agents of formula (III) are products known to those skilled in the art; they may also be in the form of mixtures of isomers, in particular racemic mixtures.

The amounts of the compounds of formulae (II) and (III) used in the process according to the invention are generally chosen such that their (III)/(II) molar ratio is greater than or equal to 1.

The temperature of the process according to the invention may vary within a wide range. The temperature of step (a) is generally from 0° to 50° C., and preferably corresponds to room temperature.

Before step (b) of the process according to the invention and when X represents a hydroxyl radical, the products of step (a) may be subjected to a reaction for protection of the hydroxyl groups, by reaction with a protective agent chosen from acid anhydrides, acid halides and chlorosilanes, the reaction being followed, after isolation of the compounds according to the step (b), by a hydrolysis or a hydrogenolysis.

The protective agents used in the process of the present invention are preferably chosen from acetic anhydride, benzoyl chloride, benzyl chloride, benzyl bromide and the chlorosilanes of formulae $ClSi(CH_3)_3$, $ClSi(CH_3)_2(tBu)$ and $ClSi(tBu)(-C_6H_5)_2$.

The compounds according to the invention may entertain various applications, in particular in cosmetic and dermatological compositions. These compositions also possess the property of forming vesicles in combination with other lipids, when they are dispersed in water.

The subject of the present invention thus includes the use of compositions of at least two compounds of formula (I) in emulsions, dispersions or in lotions. The subject of the invention also includes the use of these compounds, combined with other lipids, for the formation of lipid spherules.

The subject of the present invention also includes compositions for cosmetic or dermatological use containing at least two compounds of formula (I).

Another subject of the invention is a process for the cosmetic treatment of the skin, the hair, the nails or the eyelashes which comprises applying to the latter a sufficient amount of at least two compounds of formula (I).

The compositions according to the invention may be in the form of emulsions (milk or cream), aqueous-alcoholic compositions, oily or oleo-alcoholic lotions, gels, dispersions or solid sticks, sprays or aerosol foam.

According to the invention, the compounds of formula (I) preferably represent from 0.005% to 20%, more preferably from 0.01 to 10%, of the total weight of the composition.

The compositions are, for example, emollient lotions, milks or creams, milks or creams for skin or hair care, creams, lotions or milks for removing make-up, foundation bases, antisun lotions, milks or creams, artificial tanning lotions, milks or creams, shaving creams or foams, aftershave lotions, shampoos, lipsticks, mascaras or nail varnishes.

These compositions may also be provided in the form of lipsticks intended either to color the lips or to avoid chapping, or make-up products for the eyes or powders and foundations for the face.

When the compositions according to the invention are provided in the form of emulsions of the water-in-oil or oil-in-water type, the fatty phase comprises a mixture of at least two compounds of formula (I) with at least one oil, and possibly one other fatty substance.

The fatty phase of the emulsions may preferably constitute from 5 to 60% of the total weight of the emulsion.

The aqueous phase of the said emulsions preferably constitutes from 30 to 85% of the total weight of the emulsion.

The proportion of emulsifying agent may preferably be from 1 to 20% and more preferably from 2 to 12% of the total weight of the emulsion.

When the compositions according to the invention are provided in the form of oily, oleo-alcoholic or aqueous-alcoholic lotions, they may constitute, for example, sunscreen lotions containing a screening agent which absorbs UV rays or skin-softening lotions; the oily lotions may additionally constitute foaming oils containing an oleo-soluble surfactant, bath oils, etc.

Among the main adjuvants which may be present in the compositions according to the invention there may be mentioned fatty substances such as mineral, animal or vegetable oils or waxes, fatty acids, fatty acid esters such as fatty acid triglycerides having from 6 to 18 carbon atoms, and fatty alcohols; emulsifying agents such as oxyethylenated fatty alcohols or polyglyceryl alkyl ethers; solvents such as lower monoalcohols or polyalcohols containing from 1 to 6 carbon atoms, or alternatively water.

The mono- or polyalcohols more particularly preferred are chosen from ethanol, isopropanol, propylene glycol, glycerol and sorbitol.

By way of fatty substance and among the mineral oils there may be mentioned liquid petrolatum; among the animal oils there may be mentioned whale, shark, seal, menhaden, halibut liver, cod, tuna, tortoise, ox foot, horse foot, sheep foot, mink, otter, marmot etc. oils; among the vegetable oils there may be mentioned almond, wheat germ, olive, corn germ, jojoba, sesame, sunflower, palm, walnut, karite, shorea, macadamia, blackcurrant seed oils and the like.

Among the fatty acid esters, it is possible to use saturated or unsaturated $C_{12}$ to $C_{22}$ acid esters of lower alcohols such as isopropanol or glycerol or of saturated or unsaturated, linear or branched $C_8$ to $C_{22}$ fatty alcohols or alternatively of $C_{10}$—$C_{22}$ 1,2-alkanediols.

There may also be mentioned as fatty substance petrolatum, paraffin, lanolin, hydrogenated lanolin, tallow, acetylated lanolin and silicone oils.

Among the waxes there may be mentioned Sipol wax, lanolin wax, beeswax, candelilla wax, microcrystalline wax, carnauba wax, spermaceti, cocoa butter, karite butter, silicone waxes, hydrogenated oils which are solid at 25° C., sucroglycerides, and the oleates, myristates, linoleates and stearates of calcium, magnesium and aluminium.

Among the fatty alcohols there may be mentioned lauryl, cetyl, myristyl, stearyl, palmityl and oleyl alcohol and guerbet alcohols such as 2-octyl-dodecanol, 2-decyltetradecanol or 2-hexyldecanol.

By way of emulsifying agents and among the polyoxyethylenated fatty alcohols there may be mentioned lauryl, cetyl, stearyl and oleyl alcohol containing from 2 to 20 mol of ethylene oxide, and among the polyglyceryl alkyl ethers there may be mentioned the $C_{12}$—$C_{18}$ alcohols containing from 2 to 10 mol of glycerol.

It may also be useful to employ thickening agents such as cellulose derivatives, polyacrylic acid derivatives, guar gum, carob gum or xanthan gum.

The composition according to the invention may also contain adjuvants commonly used in cosmetics or in dermatology and in particular moisturizing products, softeners, products for treating skin complaints, sunscreen agents, germicides, dyes, preserving agents, fragrances and propellants.

When the compositions according to the invention are dispersions, they may be dispersions of at least two compounds of formula (I) in water in the presence of surfactant or alternatively aqueous dispersions of lipid spherules, comprising organized molecular layers enclosing an encapsulated aqueous phase, these layers comprising at least one mixture of isomers of compounds of formula (I) combined with at least one other lipid compound.

To this effect, there may be mentioned as lipid compounds long-chain alcohols and diols, sterols such as cholesterol, phospholipids, cholesteryl sulphate and phosphate, long-chain amines and their quaternary ammonium derivatives, dihydroxyalkylamines, polyoxyethylenated fatty amines, long-chain amino alcohol esters, their salts and quaternary ammonium derivatives, phosphoric esters of fatty alcohols such as dicetyl hydrogen phosphate or its sodium salt and alkyl sulphates such as sodium cetyl sulphate, fatty acids in the form of salts or alternatively lipids of the type of those described in French patent Nos. 2,315,991, 1,477,048 and 2,091,516 or in international patent applications WO 83/01 571 and WO 92/08685, the disclosures of which are specifically incorporated by reference.

It is possible, for example, to use as other lipids, lipids containing a saturated or unsaturated, branched or linear long lipophilic chain containing 12 to 30 carbon atoms, for example an oleyl, lanolyl, tetradecyl, hexadecyl, isostearyl, lauryl or alkylphenyl chain. The hydrophilic group of these lipids may be an ionic or nonionic group. By way of nonionic groups, there may be mentioned groups derived from polyethylene glycol. It is also possible to use advantageously, as lipids forming the lamellar phase, polyglyceryl ethers such as those described in French patent Nos. 1,477,048, 2,091,516, 2,465,780 and 2,482,128, the disclosures of which are specifically incorporated herein by reference.

By way of ionic group, a group derived from an amphoteric, anionic or cationic compound may advantageously be used.

Other lipids described in international patent application WO 83/01 571, the disclosure of which is specifically incorporated herein by reference, as capable of being used for the formation of vesicles are glycolipids, such as lactosylceramide, galactocerebroside, gangliosides and trihexosylceramide, as well as phospholipids, such as phosphatidylglycerol and phosphatidylinositol.

Another subject of the present invention is thus a dispersion of lipid spherules consisting of organized molecular layers of at least two compounds of formula (I) and of lipid defined above containing an aqueous phase to be encapsulated.

The continuous phase of the dispersion which surrounds the spherules is an aqueous phase.

The spherules in dispersion generally have a diameter of from 0.05 $\mu$m to 5 $\mu$m.

The encapsulated aqueous phase in the spherules may be water or an aqueous solution of an active substance and is, in this case, preferably iso-osmotic relative to the continuous phase of the dispersion.

The spherules may be obtained in particular according to the process described in French patent 2,315,991,the disclosure of which is specifically incorporated herein by reference, according to which a dispersion of spherules is prepared, comprising organized molecular layers containing an aqueous phase to be encapsulated, by placing together, on the one hand, isomeric mixtures of compounds of formula (I) associated with one or more lipid(s) defined above and, on the other hand, the aqueous phase to be encapsulated in the spherules, by stirring in order to ensure mixing and to obtain a lamellar phase, by subsequently adding a dispersion liquid in an amount greater than the amount of lamellar phase obtained and by shaking vigorously for a period ranging from 15 minutes to approximately 3 hours.

Another preparation process involves using the process referred to as REV (reverse-phase evaporation vesicle), described in Proc. Natl. Acad. Sci. USA., Vol. 75, No. 9, pages 4194–4198 (1978), by Szoka and Papahadjopoulos, the disclosure of which is specifically incorporated herein by reference.

It is also possible to carry out the process which comprises the sequence of steps comprising dissolving at least one lipid in at least one water-immiscible organic solvent; adding the organic phase thus obtained to an aqueous phase; forming a dispersion of the two phases with vigorous stirring, it being possible for the size of the vesicles to be controlled by varying the stirring speed during this mixing of the phases; evaporating the solvent(s) with vigorous stirring; and, where appropriate, concentrating the dispersion.

The active substances may be substances of pharmaceutical or food interest or substances having a cosmetic activity. When they are water-soluble, they are in the aqueous phase encapsulated inside the vesicles.

The water-soluble substances having a cosmetic and/or pharmaceutical activity may be products intended for the care or treatment of skin or hair, for example, such as moistening agents, such as glycerol, sorbitol, pentaerythritol or pyrrolidonecarboxylic acid and its salts; artificial tanning agents, such as dihydroxyacetone, erythrulose, glyceraldehyde or γ-dialdehydes, such as tartaric aldehyde, these compounds possibly being associated with dyes; water-soluble sunscreen agents; antiperspirants, deodorants, astringents, freshening, tonic, cicatrizing, keratolytic and depilatory products, or perfumed waters; plant tissue extracts, such as polysaccharides; water-soluble dyes; anti-dandruff agents; anti-seborrhoeic agents, or oxidizing agents, such as bleaching agents, for instance hydrogen peroxide; and reducing agents, such as thioglycolic acid and its salts.

Vitamins, hormones, enzymes such as superoxide dismutase, vaccines, anti-inflammatory agents such as hydrocortisone, antibiotics, bactericides, cytotoxic agents and anti-tumor agents may also be mentioned.

When the active substances are liposoluble, they are found incorporated within the lamellae of the vesicles. They may be chosen from the group formed by liposoluble sunscreen agents, substances intended for improving the condition of dry or senile skin, tocopherols, vitamins E, F or A and their esters, retinoic acid, antioxidants, essential fatty acids, glycyrrhetinic acid, keratolytic agents and carotenoids.

The dispersions of lipid spherules have the advantage of conveying active substances, which are thus masked and protected with respect to the various degrading agents: oxidizing agents and more generally compounds which are reactive towards encapsulated active substances. The penetration and the fixing of the active substances may be modulated by varying the size of the spherules and their electric charge. The action of these active substances may also be delayed in this way (retarding effect).

The subject of the invention further comprises the use in cosmetics of an aqueous dispersion of spherules which comprises organized molecular layers of at least two compounds of formula (I) associated with other lipids containing an aqueous phase to be encapsulated, in particular for treating the skin.

The subject of the invention is also the use of such a dispersion of lipid spherules in dermatology or in the food industry.

In the following text and in the preceding text, the percentages are given by weight, except where otherwise mentioned.

The examples which follow are given by way of illustration and with no limitation.

THF means tetrahydrofuran and A.M. means active material.

EXAMPLE 1

Preparation of 2-N-hexadecanoylaminooctadecane-1,3,4-triol (2 D,L-ribo isomers)

2-Aminooctadecane-1,3,4-triol (2 D,L-ribo isomers, 450 mg, $1.4 \times 10^{-3}$ mol) was suspended in 25 ml of tetrahydrofuran (THF). Palmitoyl chloride (390 mg, $1.4 \times 10^{-3}$ mol) was added in a single portion. Triethyl-amine (145 mg, about $1.4 \times 10^{-3}$ mol) was run in slowly. After 4 hours, no more amine remained. On addition of water to the reaction medium, a precipitate was obtained.

After filtration, washing and drying, 730 mg of white solid were obtained (yield: 94%).

The solid was recrystallized from methanol and THF, and 400 mg of white crystals were thus recovered (yield: 51%). The $^{13}$C NMR, the mass spectrum, and the elemental analysis of the product obtained were in accordance with the expected product of melting point 124°–125° C.; 2-N-hexadecanoylaminooctadecane-1,3,4-triol (2 D,L-ribo isomers)

EXAMPLE 2

Preparation of 2-N-hydroxyhexadecanoylaminooctadecane-1,3,4-triol(4 isomers)

D,L-2-Hydroxyhexadecanoic acid (2 g, $7.5 \times 10^{-3}$ mol) was suspended in 50 ml of ethyl acetate. N-Hydroxysuccinimide (0.8 g, $7.5 \times 10^{-3}$ mol) and dicyclohexylcarbodiimide (1.5 g, $7.5 \times 10^{-3}$ mol) were added rapidly. The mixture was stirred for 2 hours at room temperature. The dicyclohexylurea was filtered off. The solid obtained was resuspended in 20 ml of THF, and this solution was poured into a mixture of 2-aminooctadecane-1,3,4-triol (2 D,L-ribo isomers, 2.4 g, $7.5 \times 10^{-3}$ mol) and 100 ml of THF, and the solution was brought to reflux. After refluxing for 1 hour, the reaction was stopped, and the mixture was allowed to cool to room temperature. 50 g of silica were added directly to the reaction medium.

After filtration and evaporation to dryness, 3.8 g of white solid were obtained (88% yield). The product obtained was recrystallized from an ethanol/water mixture (9/1). 2.1 g of white crystals were thus obtained (49% yield). The $^{13}$C NMR spectrum and the elemental analysis of the product obtained were in accordance with the expected product of melting point 134°–136° C.: 2-N-hydroxyhexadecanoylaminooctadecane-1,3,4-triol(4 isomers).

EXAMPLE 3

Preparation of 2-N-docosanoylaminooctadecane-1,3,4-triol (2 D,L-ribo isomers)

Behenic acid (530 mg, $1.6 \times 10^{-3}$ mol) was dissolved in 10 ml of ethyl acetate. N-hydroxy-succinimide (175 mg, $1.6 \times 10^{-3}$ mol) and dicyclohexylcarbodiimide (325 mg, $1.6 \times 10^{-3}$ mol) were added rapidly. The mixture was stirred at room temperature for 2 hours, the dicyclohexylurea was filtered off, and the filtrate was evaporated to dryness.

The solid obtained was resuspended in 5 ml of THF and poured rapidly into a solution of 2-aminooctadecane-1,3,4-triol (2 D,L-ribo isomers, 500 mg, $1.6 \times 10^{-3}$ mol, 5 ml of THF) at reflux. This reflux was maintained for 1 hour.

The product was purified by chromatography, the reaction medium being placed directly on the column (the eluent being a mixture of 1,2-dichloroethane and isopropanol (80/20)). 150 mg of white solid were thus isolated. The $^{13}$C NMR spectrum and the elemental analysis of the product obtained were in accordance with the expected product of melting point 123°–124° C.: 2-N-docosanoylaminooctadecane-1,3,4-triol (2 D,L-ribo isomers)

EXAMPLE 4

Preparation of 2-N-hexadecanoylaminooctadecane-1,3,4-triol (8 isomers)

0.5 g of 2-aminooctadecane-1,3,4-triol hydrochloride (8 isomers, $1.4 \times 10^{-3}$ mol) was dissolved in 25 ml of THF. One equivalent of triethylamine was added rapidly, followed by 0.39 g of palmitoyl chloride ($1.4 \times 10^{-3}$ mol). Lastly, a second equivalent of base was added.

After stirring for 30 minutes at room temperature and addition of two volumes of water, a white precipitate was obtained. This precipitate was filtered off, washed with water, and then dried under vacuum in the presence of $P_2O_5$.

After recrystallization from ethyl acetate, 0.4 g of white solid was obtained (78% yield). The $^{13}$C NMR spectrum and the elemental analysis of the product obtained were in accordance with the expected product: 2-N-hexadecanoylaminooctadecane-1,3,4-triol (8 isomers)

EXAMPLE 5

Preparation of 2-N-(2-hydroxyhexadecanoylaminooctadecane-1,3,4-triol (16 isomers)

Process A 2 g of D,L-2-hydroxyhexadecanoic acid ($7.5 \times 10^{-3}$ mol) were dissolved in 50 ml of ethyl acetate. 0.8 g of N-hydroxysuccinimide ($7.5 \times 10^{-3}$ mol) and 1.5 g of dicyclohexylcarbodiimide ($7.5 \times 10^{-3}$ mol) were added rapidly. The mixture was stirred at room temperature for 2 hours. The dicyclohexylurea was filtered off, and the solution was concentrated under vacuum. The solid thus obtained was redissolved in 20 ml of THF. This solution was poured into a reactor containing 2.4 g of 2-aminooctadecane-1,3,4-triol (8 isomers, $7.5 \times 10^{-3}$ mol) dissolved in 100 ml of refluxing THF. After refluxing for one hour, the mixture was evaporated to dryness.

The product thus obtained was purified by chromatography on a column of silica (the eluent being: 1,2-dichloroethane (9)/methanol(1)). 1 g of white solid was isolated. The mass spectrum of the product obtained corresponded to the expected structure of melting point 138°–140° C.: 2-N-(2-hydroxyhexadecanoylaminooctadecane-1,3,4-triol (16 isomers)

Process B 37 g of 2-aminooctadecane-1,3,4-triol (8 isomers, $1.16 \times 10^{-1}$ mol) were dissolved in 300 ml of THF. When the medium was homogeneous, it was cooled to about 20° C. 41.3 g of D,L-2-bromohexadecanoyl chloride ($1.16 \times 10^{-1}$ mol) and 16.5 ml of triethylamine ($1.16 \times 10^{-1}$ mol) were added rapidly. The mixture was heated at 50° C. for 2 hours. The mixture was poured into 2 liters of ice-cold water with stirring. It was left stirring for 1 hour. The product was filtered off, washed with water and then dried.

73 g of the bromo derivative obtained ($1.15 \times 10^{-1}$ mol) were then dissolved in 250 ml of N-methylpyrrolidone. 22.5 g of potassium acetate ($2.3 \times 10^{-1}$ mol) were added. The mixture was heated at 90° C. for 4 hours. It was cooled and poured into 2 liters of ice-cold water. The product was filtered off rapidly, washed again and then dried.

46 g of acetate obtained ($7.3 \times 10^{-2}$ mol) were dissolved in 350 ml of hot methanol. The mixture was allowed to cool to room temperature, and 2.2 ml of a 30% solution of sodium methoxide in methanol were added. The reaction medium was stirred for 4 hours. The product was filtered off, dried and recrystallized from a minimum of heptane. 20 g of very slightly beige solid were obtained. The elemental analysis of the product obtained was in accordance with the expected product of melting point 138°–140° C. (product equivalent to the product obtained by process A): 2-N-(2-hydroxyhexadecanoylaminooctadecane-1,3,4-triol (16 isomers)

EXAMPLE 6

This example comprises various formulations for the care or treatment of the hair with compounds of the above examples.

| Shampoo | |
|---|---|
| Sodium lauryl ether sulphate (28% A.M.) | 75 g |
| Coconut acid monoisopropanolamide sold by Albright and Wilson under the name Empilan CIS | 1 g |
| Compound of Example 5 | 1 g |
| Water q.s. | 100 g |

The shampoo thus formulated was of clear appearance.

| Rinse-out conditioner | |
|---|---|
| 1-Methyl-2-tallow-3-sulphamidoethylimidazolium methosulphate/propylene glycol (75/25) sold by Witco under the name Rewoquat W75PG | 2 g A.M. |
| Compound of Example 5 | 0.5 g |
| Oxyethylenated mixture of cetyl alcohol and cetylstearyl alcohol | 3 g |
| Preserving agent, fragrance | |
| Water q.s. | 100 g |
| Spontaneous pH of 5.2 | |

| Shampoo | |
|---|---|
| Sodium lauryl ether sulphate (28% A.M.) | 60 g |
| Cocoylbetaine | 9 g |
| Compound of Example 4 | 0.5 g |
| Preserving agent, fragrance | |
| Water q.s. | 100 g |
| HCl q.s. | pH 6 |

The shampoo thus formulated was opaque.

| Rinse-out disentangling lotion | |
|---|---|
| 80% Behenyltrimethylammonium chloride in a water/isopropanol mixture (15/85) sold by Toho (Catinal DC50 ®) | 0.5 g A.M. |
| Compound of Example 4 | 0.1 g |
| Preserving agent, fragrance | |
| Water q.s. | 100 g |
| NaOH q.s. | pH 5.5 |

EXAMPLE 7

This example comprises various formulations for the care or treatment of the skin with compounds of the above examples.

| Moisturizing oil-in-water emulsion | |
|---|---|
| Corn germ oil | 2 g |
| Glyceryl monostearate | 3 g |
| Polyethylene glycol 400 | 3 g |

| -continued | |
|---|---|
| Carbopol 941 ® sold by Goodrich | 0.2 g |
| Isopropyl myristate | 3.0 g |
| Compound of Example 4 | 0.1 g |
| Cetyl alcohol | 3.0 g |
| Stearyl alcohol | 3.0 g |
| NaOH | 0.008 g |
| Propylene glycol | 5.0 g |
| Preserving agents | 0.3 g |
| Water q.s. | 100 g |
| Moisturizing water-in-oil emulsion | |
| Liquid petrolatum | 10.0 g |
| Protegin X sold by Goldschmidt | 20.0 g |
| Sunflower oil | 15.0 g |
| Aromatic composition | 1.0 g |
| Compound of Example 5 | 0.05 g |
| Magnesium sulphate | 0.5 g |
| Glycerol | 5.0 g |
| Cetrol HE sold by Henkel | 4.0 g |
| Preserving agents | 0.3 g |
| Water q.s. | 100 g |
| Aqueous gel | |
| Carbopol 940 ® sold by Goodrich | 0.6 g |
| Transcutol ® sold by Gattefosse | 5.0 g |
| Triethanolamine | 0.3 g |
| Preserving agents | 0.3 g |
| Propylene glycol | 3.0 g |
| NaOH | 0.007 g |
| Compound of Example 4 | 0.1 g |
| Water q.s. | 100 g |
| Cream with nonionic liposomes | |
| Carbopol 940 ® sold by Goodrich | 0.2 g |
| Transcutol ® sold by Gattefosse | 3.0 g |
| Triethanolamine | 0.2 g |
| Preserving agents | 0.3 g |
| Polyglyceryl-3 cetyl ether | 3.8 g |
| β-sitosterol | 3.8 g |
| Dicetyl phosphate | 0.4 g |
| NaOH | 0.007 g |
| Compound of Example 5 | 0.15 g |
| Sunflower oil | 35.0 g |
| Fragrance | 0.3 g |
| Water q.s. | 100 g |

EXAMPLE 8

A comparative test was performed on the effects on the smoothness of the hair of a solution containing 1% of the compound of Example 4 in tetrahydrofuran (THF), relative to a control consisting of THF, or to a solution containing, in place of the compound according to the invention, either the pure isomer (D-ribo form) corresponding to the compound of Example 4 (compound A) or the compound of Example 1 of the European patent application published under the No. 0,500,437 owned by the present assignee (compound B).

This test determines the coefficient of friction of the hair by measuring the force to apply to a control mass in order to make it slide at constant speed on two hairs stretched out in parallel. The measurement is made by sliding the mass from the root to the tip of the hairs (R→T) and vice versa (T→R).

The results are collated in Table 1 below.

TABLE 1

| Composition | Treatment | Natural hair | | Bleached hair | |
|---|---|---|---|---|---|
| | | R→T | T→R | R→T | T→R |
| THF | non-rinsed | 0.186 ± 0.006 | 0.246 ± 0.004 | 0.181 ± 0.003 | 0.235 ± 0.007 |
| THF | rinsed | 0.151 ± 0.006 | 0.220 ± 0.006 | 0.188 ± 0.006 | 0.256 ± 0.004 |
| Compound B | non-rinsed | 0.130 ± 0.003 | 0.225 ± 0.005 | 0.136 ± 0.006 | 0.217 ± 0.008 |
| Compound B | rinsed | 0.106 ± 0.006 | 0.179 ± 0.005 | 0.119 ± 0.006 | 0.202 ± 0.006 |
| Compound A | non-rinsed | 0.000 | 0.000 | 0.000 | 0.000 |
| Compound A | rinsed | 0.125 ± 0.004 | 0.214 ± 0.004 | 9.191 ± 0.004 | 0.264 ± 0.012 |
| Example 4 | non-rinsed | 0.089 ± 0.003 | 0.143 ± 0.003 | 0.009 ± 0.006 | 0.147 ± 0.006 |
| Example 4 | rinsed | 0.095 ± 0.004 | 0.147 ± 0.004 | 0.085 ± 0.002 | 0.155 ± 0.004 |

Application of the compound according to the invention (Example 4) allowed a marked decrease in the coefficient of friction, thus demonstrating an improvement in the smoothness or in the disentangling of the hair.

Compound A, which corresponds to the pure isomer, was placed on the hair (no possibility of smoothing out) and thus made the measurement according to this test impossible during a non-rinsed treatment; this result thus shows one of the drawbacks of the products in the form of a single isomer.

EXAMPLE 9

Measurement of the imperceptible water loss (IWL)

This measurement is made using an evaporimeter (Servomed) which quantitatively determines water evaporation, that is to say diffusional water transport, from a sample of previously delipidized stratum corneum which forms a stopper in a cylindrical capsule containing water, the entire assembly being placed in a chamber at controlled temperature and relative humidity.

Sensors allow the partial vapor pressure of water to be measured at two points located at different distances from the sample.

The partial vapor pressure of water is thus determined between the two points, and thus the rate of evaporation in accordance with Fick's law.

A comparative test was performed of the effects on the IWL of a solution containing the compound of Example 2 or 4 in tetrahydrofuran (THF) relative to a solution containing, in place of the compound according to the invention, either the pure isomer (D-ribo form) corresponding to the compound of Example 4 (compound A), or the compound of Example 1 of the European patent application published under the No. 0,500,437 filed by the Applicant (compound B).

The results are collated in Table 2 below.

TABLE 2

| Compound | Composition (concentration) | I.W.L. 20 H (%) |
|---|---|---|
| Compound B | 1.5% in THF | −8 ± 1 |
| Example 4 | 1.5% in THF | −15 ± 2 |
| Compound A | 1% in THF | 0 ± 2 |
| Example 4 | 1% in THF | −9 ± 2 |
| Compound B | 2% in THF | −17 ± 3 |
| Example 2 | 2% in THF | −31 ± 2 |

It is thus observed from each of the three sets of comparisons that the application of the compounds according to the invention made it possible to reduce significantly the evaporation of the water contained in the stratum corneum, thus demonstrating, for the compounds according to the invention, improved barrier properties and properties of water permeability of the stratum corneum.

What is claimed is:

1. At least two compounds corresponding to the formula:

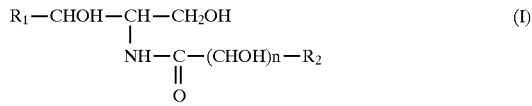

$$R_1-CHOH-CH-CH_2OH \quad\quad (I)$$
$$\quad\quad\quad\quad\quad | $$
$$\quad\quad\quad NH-C-(CHOH)_n-R_2$$
$$\quad\quad\quad\quad\; \|$$
$$\quad\quad\quad\quad\; O$$

in which:

$R_1$ denotes a saturated or unsaturated $C_{10}$ to $C_{25}$ hydroxylated hydrocarbon radical;

n is equal to 0 or 1;

$R_2$, when n is equal to 1, denotes a linear or branched, saturated or unsaturated $C_1$ to $C_{31}$ hydrocarbon radical;

$R_2$, when n is equal to 0, denotes a linear or branched, saturated or unsaturated $C_2$ to $C_{31}$ hydrocarbon radical;

said at least two compounds being in the form of a mixture of at least two isomers at least on the amino alcohol part of the formula (I).

2. The compounds according to claim 1, wherein, when $R_1$ denotes a saturated and hydroxylated hydrocarbon radical, the hydroxyl radical is in an α position relative to the carbon of the —CHOH— group.

3. The compounds according to claim 1, wherein, when $R_1$ denotes an unsaturated and hydroxylated hydrocarbon radical, $R_1$ has an ethylenic radical in an α position relative to the carbon of the —CHOH— group.

4. The compounds according to claim 3, wherein a hydroxyl radical contained in $R_1$ is in an α-position relative to said ethylenic radical in $R_1$.

5. The compounds according to claim 4, wherein said hydroxy radical contained in $R_1$ is the only hydroxy radical in $R_1$.

6. The compounds according to claim 1, wherein $R_1$ denotes a $C_{12}$ to $C_{23}$ hydrocarbon radical.

7. The compounds according to claim 1, wherein $R_2$ denotes a linear hydrocarbon radical.

8. The compounds according to claim 7, wherein $R_2$ denotes a $C_2$ to $C_{25}$ hydrocarbon radical.

9. The compounds according to claim 1, wherein said compounds are in the form of a mixture of at least 4 isomers.

10. The compounds according to claim 1, wherein said compounds are selected from 2-N-docosanoylaminooctadecane-1,3,4-triol, 2-N-(2-hydroxyhexadecanoyl)aminooctadecane-1,3,4-triol and 2-N-hexadecanoylaminooctadecane-1,3,4-triol.

11. A process for the preparation of at least two compounds of formula (I) according to claim 1, said process comprising:

(a) acylating at least two compounds in the form of a mixture of isomers of the following formula (II):

in which formula (II), $R_1$ has the meaning given in claim 1, or of at least one reactive derivative of a compound of formula (II), with at least one acylating agent of following formula (III):

$$R_2—(CHX)_n—CO—A \qquad (III)$$

in which formula (III), $R_2$ and n have the meanings given in claim 1 and X represents a hydroxyl radical, a halogen atom, or a radical of formula OB capable of forming an OH group; A is a halogen atom, a radical of formula —O—COO—$R_5$, a radical of formula $OR_6$, a group

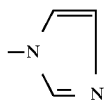

or a group

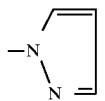

where $R_5$ is a $C_2$ to $C_8$ hydrocarbon radical and $R_6$ is a $C_1$ to $C_8$ hydrocarbon radical,

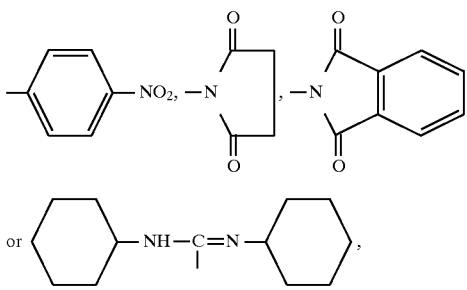

(b) isolating the at least two compounds obtained, and
(c) optionally, when X is other than a hydroxyl radical, hydrolyzing or hydrogenolyzing said at least two compounds obtained to convert the group OB into a hydroxyl radical, optionally preceded, when X is a halogen atom, by a step of substitution of X with a group OB.

12. A process according to claim 11, wherein when X is a halogen atom, X represents Br, Cl or I.

13. A process according to claim 11, further comprising, when X is the hydroxyl radical,
  after (a) acylating and before (b) isolating the at least two compounds (I) obtained, the step of protecting the hydroxyl groups by reacting said at least one acylated compound with a protective agent selected from acid anhydrides, acid halides and chlorosilanes, and
  after (b) isolating, hydrolyzing or hydrogenolyzing said at least two isolated compounds.

14. A process according to claim 13, wherein said protective agent is acetic anhydride, benzoyl chloride, benzyl chloride, benzyl bromide, or a chlorosilane of formula $ClSi(CH_3)_3$, $ClSi(CH_3)_2(tBu)$ or $ClSi(tBu)(—C_6H_5)_2$.

15. A process according to claim 11, wherein the radical OB of the acylating agent is an acetate, benzoate, benzyloxy, —$OSi(CH_3)_3$, —$OSi(CH_3)_2$(t-butyl), or —OSi(t-butyl)(—$C_6H_5)_2$.

16. A process according to claim 11, wherein said process is carried out in a solvent selected from tetrahydrofuran, pyridine, 1,2-dimethoxyethane, dimethylformamide, dichloromethane and tert-butyl methyl ether.

17. A process according to claim 11, wherein the group A of the acylating agent of formula (III) is selected from the following groups:
  —Cl, a radical of formula —O—COO—$C_2H_5$, a radical of formula —$OCH_3$, a radical of formula —$OC_2H_5$,

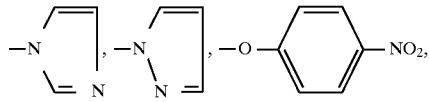

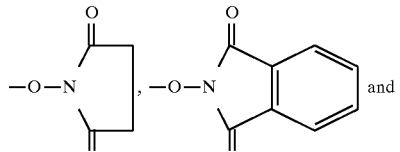

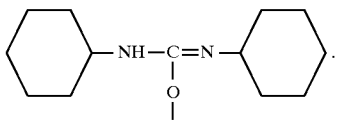

* * * * *